US009334205B2

(12) United States Patent
Tirtowidjojo et al.

(10) Patent No.: US 9,334,205 B2
(45) Date of Patent: May 10, 2016

(54) PROCESS FOR THE PRODUCTION OF CHLORINATED PROPANES AND PROPENES

(71) Applicant: Blue Cube IP LLC, Midland, MI (US)

(72) Inventors: Max Markus Tirtowidjojo, Lake Jackson, TX (US); Matthew Lee Grandbois, Midland, MI (US); William J. Kruper, Sanford, MI (US); Edward M. Calverley, Midland, MD (US); David Stephen Laitar, Midland, MI (US); Kurt Frederick Hirksekorn, Midland, MI (US)

(73) Assignee: Blue Cube IP LLC, Midland, MI (US)

( * ) Notice: Subject to any disclaimer, the term of this patent is extended or adjusted under 35 U.S.C. 154(b) by 0 days.

(21) Appl. No.: 14/365,143

(22) PCT Filed: Dec. 12, 2012

(86) PCT No.: PCT/US2012/069230
§ 371 (c)(1),
(2) Date: Jun. 13, 2014

(87) PCT Pub. No.: WO2013/090421
PCT Pub. Date: Jun. 20, 2013

(65) Prior Publication Data
US 2014/0371494 A1    Dec. 18, 2014

Related U.S. Application Data

(60) Provisional application No. 61/570,028, filed on Dec. 13, 2011, provisional application No. 61/583,799, filed on Jan. 6, 2012.

(51) Int. Cl.
C07C 17/013    (2006.01)
C07C 17/23    (2006.01)
C07C 17/10    (2006.01)
C07C 17/25    (2006.01)

(52) U.S. Cl.
CPC .............. *C07C 17/013* (2013.01); *C07C 17/10* (2013.01); *C07C 17/23* (2013.01); *C07C 17/25* (2013.01)

(58) Field of Classification Search
CPC ...... C07C 17/013; C07C 17/23; C07C 17/10; C07C 17/25
USPC ................. 570/101, 230, 234, 235, 254, 261
See application file for complete search history.

(56) References Cited

U.S. PATENT DOCUMENTS

| 2,119,484 | A | 5/1938 | Levine |
| 2,179,378 | A | 11/1939 | Metzger |
| 2,207,193 | A | 7/1940 | Groll |
| 2,299,441 | A | 10/1942 | Vaughn |
| 2,302,228 | A | 11/1942 | Kharasch |
| 2,370,342 | A | 2/1945 | Zellner |
| 2,378,859 | A | 6/1945 | Martin |
| 2,435,983 | A | 2/1948 | Schmerling |
| 2,449,286 | A | 9/1948 | Fairbairn |
| 2,588,867 | A | 3/1952 | Elton |
| 2,630,461 | A | 3/1953 | Sachsse et al. |
| 2,688,592 | A | 9/1954 | Skeeters |
| 2,762,611 | A | 9/1956 | Monroe |
| 2,765,359 | A | 10/1956 | Pichler et al. |
| 2,964,579 | A | 12/1960 | Weller et al. |
| 2,973,393 | A | 2/1961 | Monroe |
| 3,000,980 | A | 9/1961 | Asadorian |
| 3,094,567 | A | 6/1963 | Eaker |
| 3,112,988 | A | 12/1963 | Coldren et al. |
| 3,444,263 | A | 5/1969 | Fernald |
| 3,446,859 | A | 5/1969 | Weil |
| 3,502,734 | A | 3/1970 | Baird |
| 3,525,595 | A | 8/1970 | Hans et al. |
| 3,551,512 | A | 12/1970 | Loeffler |
| 3,558,438 | A | 1/1971 | Schoenbeck |
| 3,651,019 | A | 3/1972 | Asscher |
| 3,676,508 | A | 7/1972 | Krekeler |
| 3,819,731 | A | 6/1974 | Pitt |
| 3,823,195 | A | 7/1974 | Smith |
| 3,872,664 | A | 3/1975 | Lohmann |
| 3,914,167 | A | 10/1975 | Ivy |
| 3,920,757 | A | 11/1975 | Watson |
| 3,926,758 | A | 12/1975 | Smith |
| 3,948,858 | A | 4/1976 | Weirsum |
| 3,954,410 | A | 5/1976 | Pohl et al. |
| 4,038,372 | A | 7/1977 | Colli |
| 4,046,656 | A | 9/1977 | Davis et al. |
| 4,051,182 | A | 9/1977 | Pitt |

(Continued)

FOREIGN PATENT DOCUMENTS

CH    609022    6/1974
CN    101215220    7/2008

(Continued)

OTHER PUBLICATIONS

Bai et al., "Isomerization of Tetrachloropropene to Promote Utilization Ratio of Triallate Raw Materials" Petrochemical Technology & Application, 2007, 25(1).
Boualy et al., "Kharasch Addition of Tetrachloromethane to Alkenes Catalyzed by Metal Acetylacetonates", Catalysis Communications, 2011, pp. 1295-1297, vol. 12.
Chai et al., "Study of Preparation of 1,1,1,3-tetrachloropropane", Zhejiang Huagong Industry, 2010, pp. 1-3, 41(5).
Cristiano et al., Tetraalkylphosphonium Trihalides. Room Temperature Ionic Liquids as Halogenation Reagents, J. Org. Chem., 2009, pp. 9027-9033, vol. 74.
Evstigneev et al., "Initiated Chlorination of Tetrachloropropane", Khim. Prom., 1984, pp. 393-394, 16(7).
Fields et al., "Thermal Isomerization of 1,1-dichlorocyclopropanes", Chemical Communications, Jan. 1, 1967, 1081, No. 21.

(Continued)

*Primary Examiner* — Shailendra Kumar
(74) *Attorney, Agent, or Firm* — Polsinelli PC

(57) ABSTRACT

Processes for the production of chlorinated propanes and propenes are provided. The present processes comprise catalyzing at least one chlorination step with one or more regioselective catalysts that provide a regioselectivity to one chloropropane of at least 5:1 relative to other chloropropanes.

16 Claims, No Drawings

(56) References Cited

U.S. PATENT DOCUMENTS

| | | |
|---|---|---|
| 4,319,062 A | 3/1982 | Boozalis et al. |
| 4,513,154 A | 4/1985 | Kurtz |
| 4,535,194 A | 8/1985 | Woodard |
| 4,614,572 A | 9/1986 | Holbrook |
| 4,644,907 A | 2/1987 | Hunter |
| 4,650,914 A | 3/1987 | Woodard |
| 4,661,648 A | 4/1987 | Franklin |
| 4,702,809 A | 10/1987 | Mueller |
| 4,714,792 A | 12/1987 | Mueller |
| 4,716,255 A | 12/1987 | Mueller |
| 4,726,686 A | 2/1988 | Wolf |
| 4,727,181 A | 2/1988 | Kruper |
| 4,849,554 A | 7/1989 | Cresswell et al. |
| 4,894,205 A | 1/1990 | Westerman |
| 4,902,393 A | 2/1990 | Mueller |
| 4,999,102 A | 3/1991 | Cox |
| 5,057,634 A | 10/1991 | Webster |
| 5,132,473 A | 7/1992 | Furutaka |
| 5,171,899 A | 12/1992 | Furutaka |
| 5,178,844 A | 1/1993 | Carter et al. |
| 5,246,903 A | 9/1993 | Harley |
| 5,254,771 A | 10/1993 | Cremer |
| 5,254,772 A | 10/1993 | Dukat |
| 5,254,788 A | 10/1993 | Gartside |
| 5,262,575 A | 11/1993 | Dianis |
| 5,315,044 A | 5/1994 | Furutaka |
| 5,367,105 A | 11/1994 | Miyazaki et al. |
| 5,414,166 A | 5/1995 | Kim |
| 5,504,266 A | 4/1996 | Tirtowidjojo et al. |
| 5,684,219 A | 11/1997 | Boyce |
| 5,689,020 A | 11/1997 | Boyce |
| 5,811,605 A | 9/1998 | Tang |
| 5,895,825 A | 4/1999 | Elsheikh |
| 5,986,151 A | 11/1999 | Van Der Puy |
| 6,111,150 A | 8/2000 | Sakyu |
| 6,118,018 A | 9/2000 | Savidakis |
| 6,160,187 A | 12/2000 | Strickler |
| 6,187,976 B1 | 2/2001 | Van Der Puy |
| 6,229,057 B1 | 5/2001 | Jackson et al. |
| 6,235,951 B1 | 5/2001 | Sakyu et al. |
| 6,472,573 B1 | 10/2002 | Yamamoto |
| 6,518,467 B2 | 2/2003 | Tung et al. |
| 6,538,167 B1 | 3/2003 | Brown |
| 6,545,176 B1 | 4/2003 | Tsay |
| 6,551,469 B1 | 4/2003 | Nair |
| 6,610,177 B2 | 8/2003 | Tsay |
| 6,613,127 B1 | 9/2003 | Galloway |
| 6,683,216 B1 | 1/2004 | Zoeller |
| 6,825,383 B1 | 11/2004 | Dewkar |
| 6,924,403 B2 | 8/2005 | Barnes et al. |
| 6,958,135 B1 | 10/2005 | Filippi |
| 7,117,934 B2 | 10/2006 | Lomax |
| 7,189,884 B2 | 3/2007 | Mukhopadhyay |
| 7,226,567 B1 | 6/2007 | Olbert |
| 7,282,120 B2 | 10/2007 | Braun |
| 7,297,814 B2 | 11/2007 | Yada et al. |
| 7,345,209 B2 | 3/2008 | Mukhopadhyay |
| 7,371,904 B2 | 5/2008 | Ma et al. |
| 7,378,559 B2 | 5/2008 | Verwijs |
| 7,396,965 B2 | 7/2008 | Mukhopadhyay |
| 7,511,101 B2 | 3/2009 | Nguyen |
| 7,521,029 B2 | 4/2009 | Guetlhuber |
| 7,588,739 B2 | 9/2009 | Sugiyama |
| 7,659,434 B2 | 2/2010 | Mukhopadhyay |
| 7,674,939 B2 | 3/2010 | Mukhopadhyay |
| 7,687,670 B2 | 3/2010 | Nappa |
| 7,695,695 B2 | 4/2010 | Shin |
| 7,714,177 B2 | 5/2010 | Mukhopadhyay |
| 7,836,941 B2 | 11/2010 | Song |
| 7,880,040 B2 | 2/2011 | Mukhopadhyay |
| 7,951,982 B2 | 5/2011 | Mukhopadhyay |
| 8,058,486 B2 | 11/2011 | Merkel et al. |
| 8,058,490 B2 | 11/2011 | Strebelle |
| 8,071,825 B2 | 12/2011 | Johnson et al. |
| 8,071,826 B2 | 12/2011 | Van Der Puy |
| 8,076,521 B2 | 12/2011 | Elsheikh |
| 8,084,653 B2 | 12/2011 | Tung |
| 8,115,038 B2 | 2/2012 | Wilson |
| 8,123,398 B2 | 2/2012 | Teshima |
| 8,158,836 B2 | 4/2012 | Pigamo |
| 8,232,435 B2 | 7/2012 | Sievert |
| 8,258,353 B2 | 9/2012 | Tirtowidjojo |
| 8,258,355 B2 | 9/2012 | Merkel |
| 8,357,828 B2 | 1/2013 | Okamoto et al. |
| 8,367,867 B2 | 2/2013 | Zardi et al. |
| 8,383,867 B2 | 2/2013 | Mukhopadhyay |
| 8,395,000 B2 | 3/2013 | Mukhopadhyay |
| 8,398,882 B2 | 3/2013 | Rao |
| 8,487,146 B2 | 7/2013 | Wilson |
| 8,581,011 B2 | 11/2013 | Tirtowidjojo |
| 8,581,012 B2 | 11/2013 | Tirtowidjojo |
| 8,614,361 B2 | 12/2013 | Suzuki |
| 8,614,363 B2 | 12/2013 | Wilson et al. |
| 8,907,149 B2 | 12/2014 | Tirtowidjojo et al. |
| 8,957,258 B2 | 2/2015 | Okamoto et al. |
| 9,067,855 B2 | 6/2015 | Grandbois et al. |
| 2001/0018962 A1 | 9/2001 | Joshi et al. |
| 2002/0110711 A1 | 8/2002 | Boneberg et al. |
| 2006/0150445 A1 | 7/2006 | Redding |
| 2006/0292046 A1 | 12/2006 | Fruchey |
| 2007/0197841 A1 | 8/2007 | Mukhopadhyay |
| 2007/0265368 A1 | 11/2007 | Rao et al. |
| 2008/0021229 A1 | 1/2008 | Maughon |
| 2008/0073063 A1 | 3/2008 | Clavenna et al. |
| 2008/0118018 A1 | 5/2008 | Schrauwen |
| 2008/0207962 A1 | 8/2008 | Rao |
| 2009/0018377 A1 | 1/2009 | Boyce |
| 2009/0088547 A1 | 4/2009 | Schamshurin et al. |
| 2009/0099396 A1 | 4/2009 | Mukhopadhyay |
| 2009/0117014 A1 | 5/2009 | Carpenter |
| 2009/0203945 A1 | 8/2009 | Mukhopadhyay |
| 2009/0253946 A1 | 10/2009 | Van Der Puy |
| 2010/0041864 A1 | 2/2010 | Kadowaki et al. |
| 2010/0185029 A1 | 7/2010 | Elsheikh |
| 2010/0263278 A1 | 10/2010 | Kowoll et al. |
| 2011/0172472 A1 | 7/2011 | Sakyu |
| 2011/0218369 A1 | 9/2011 | Elsheikh et al. |
| 2011/0251425 A1 | 10/2011 | Penzel |
| 2012/0065434 A1 | 3/2012 | Nose et al. |
| 2014/0081055 A1 | 3/2014 | Tirtowidjojo |
| 2014/0179962 A1 | 6/2014 | Tirtowidjojo et al. |

FOREIGN PATENT DOCUMENTS

| | | |
|---|---|---|
| CN | 101492341 | 7/2009 |
| CN | 101544535 | 9/2009 |
| CN | 101597209 | 12/2009 |
| CN | 101913979 | 12/2010 |
| CN | 101913980 | 12/2010 |
| CN | 101955414 | 1/2011 |
| CN | 101982227 | 3/2011 |
| CN | 102001911 | 4/2011 |
| CN | 102249846 | 11/2011 |
| CN | 102351637 | 2/2012 |
| DE | 857955 | 12/1952 |
| DE | 209184 | 4/1984 |
| DE | 235631 | 5/1986 |
| DE | 102005044501 | 3/2007 |
| DE | 102010022414 | 12/2011 |
| EP | 0164798 | 12/1985 |
| EP | 0453818 | 10/1991 |
| EP | 1018366 | 12/2000 |
| EP | 1097984 | 5/2001 |
| FR | 1546709 | 11/1968 |
| GB | 471186 | 8/1937 |
| GB | 471187 | 8/1937 |
| GB | 471188 | 8/1937 |
| GB | 857086 | 12/1960 |
| GB | 1134585 | 11/1968 |
| GB | 1381619 | 1/1975 |
| GB | 1548277 | 7/1979 |
| JP | 54-079207 | 6/1979 |
| JP | S54-135712 | 10/1979 |
| JP | 08-119885 | 5/1996 |

(56) References Cited

FOREIGN PATENT DOCUMENTS

| | | |
|---|---|---|
| JP | 2001-151708 | 6/2001 |
| JP | 2001-213820 | 8/2001 |
| JP | 2006-272267 | 10/2006 |
| JP | 2007-021396 | 2/2007 |
| JP | 2008-063314 | 3/2008 |
| JP | 2009-000592 | 1/2009 |
| JP | 2009-046653 | 3/2009 |
| JP | 2011-144148 | 7/2011 |
| LU | 52247 | 12/1966 |
| SU | 899523 | 1/1982 |
| WO | 0138271 | 5/2001 |
| WO | 0138275 | 5/2001 |
| WO | 2005016509 | 2/2005 |
| WO | 2007079431 | 7/2007 |
| WO | 2007079435 | 7/2007 |
| WO | 2007096383 | 8/2007 |
| WO | 2009015304 | 1/2009 |
| WO | 2009067571 | 5/2009 |
| WO | 2009087423 | 7/2009 |
| WO | 2011060211 | 5/2011 |
| WO | 2011065574 | 6/2011 |
| WO | 2012011844 | 1/2012 |
| WO | 2012081482 | 12/2012 |
| WO | 2012166393 | 12/2012 |
| WO | 2013078035 | 5/2013 |
| WO | WO 2013-082410 | * 6/2013 |

OTHER PUBLICATIONS

Galitzenstein et al., "The Dehydrochlorination of Propylene Dichloride", Journal of the Society of Chemical Industry, 1950, pp. 298-304, vol. 69.
Gault et al., "Chlorination of Chloroform" Comptes Rendus Des Seances De L'Academie des Sciences, 1924, pp. 467-469, vol. 179.
Gerding et al, "Raman Spectra of aliphatic chlorine compounds: chloroethenes an chloropropenes", Recueil Jan. 1, 1955, pp. 957-975, vol. 74.
Hatch et al., "Allylic Chlorides. XV. Preparation and Properties of the 1,2,3Trichloropropenes". JACS, Jan. 5, 1952, pp. 123-126, vol. 74.
Hatch et al., "Allylic Chlorides. XVIII. Preparation and Properties of 1,1,3-tricholoro-2-fluoro-1-propene and 1,1,2,3-tetrachloro-1-propene". JACS, Jul. 5, 1952, pp. 3328-3330, 74(13).
Herzfelder, "Substitution in the Aliphatic Series", Berichte Der Deutschen Chemischen Gesellschaft, 26 (II), May-Aug. 1893, pp. 1257-1261, 26(2).
Ivanov et al., "Metal phthalocyanine-Catalyzed Addition of polychlorine-Containing Organic Compounds to C=C Bonds," Russian Chemical Bulletin, International Edition, Nov. 2009, pp. 2393-2396, 58(11).
Kang et al., Kinetics of Synthesis of 1,1,1,3,3-pentachlorobutane Catalyzed by Fe—FeCl3, Chemical Research and Application, Jun. 2011, pp. 657-660, 23(6).
Kharasch et al., , "Chlorinations with Sulfuryl Chloride.I. The Peroxide-Catalyzed Chlorination of Hydrocarbons", JACS, 1939, pp. 2142-2150, vol. 61.
Khusnutdinov et al., CCl4 Attachment to Olefins Catalyzed by Chromium and Ruthenium Complexes. Impact of Water as a Nucleophilic Admixture, Oil Chemistry, 2009, pp. 349-356, vol. 4.
Kruper et al., "Synthesis of alpha-Halocinnamate Esters via Solvolytic Rearrangement of Trichloroallyl Alcohols", , J Org Chem, 1991, pp. 3323-3329, vol. 56.
Leitch, "Organic Deuterium Compounds: V. The chlorination of propyne and propyne D-4", Canadian Journal of Chemistry, Apr. 1, 1953, pp. 385-386, 30(4).
Levanova et al.. "Thermocatalytic Reactions of Bromochloropropanes", Russian Journal of Physical Chemistry, Jan. 1, 1983, pp. 1142-1146, vol. 57.
Liu et al., "Progress in Synthesis of 1,1,1,3-tetrachloropropane", Guangzhou Chemicals, 2011, , pp. 41-42, 39(5).
McBee et al., , Utilization of Polychloropropanes and Hexachloroethane, Industrial and Engineering Chemistry,Feb. 1, 1941, pp. 176-181, 33(2).
Mouneyrat, "Effect of Chlorine on Propyl Chloride in the Presence of Anhydrous Aluminum Chloride" Bulletin de la Societe chimique de france, Societe francaise de chimie, vol. 3, No. 21, Jan. 1, 1899.
Munoz-Molina et al., "An Efficient, Selective and Reducing Agent-Free Copper Catalyst for the Atom-Transfer Radical Addition of Halo Compounds to Activated Olefins", Inorg. Chem., 2010, pp. 643-645, 49.
Nair et al., "Atom transfer radical addition (ATRA) of carbon tetrachloride and chlorinated esters to various olefins catalyzed by CP/Ru(PPh3)(PR3)Cl complexes", Inorganica Chimica Acta, 380 2012, 96-103.
Nguyen et al., "Condensation de chloroforme avec des olefins fluorees en milieu basique," Journal of Fluorine Chemistry, vol. 55, No. 3, Dec. 1, 1991, pp. 241-248.
Nikishin et al, "Reactions of Methanol and Ethanol with Tetrachloroethylene," N.D. Zelinskii Institute of Organic Chemistry, Academy of Sciences of the USSR, 2115-2119. Translated from Izvestiya Akademii Nauk SSSR, Seriya Khimicheskaya 1966, 12, 2188-2192.
Pozdnev et al., "Chlorination of chloroform and the conversion of methylene chloride manufacture still residues", Khim., Khim. Tekhnol. (1970) 70-4.
Rotshtein et al., "Isomer Distribution on Chlorination of Chloropropanes", Z. Organicheskoi Khimii, 2(9), pp. 1539-1542 (1966).
Semenov, "Selectivity of Photochemical Chlorination of Chloromethane in the Liquid Phase", Prikladnei Khimii, vol. 58, No. 4, pp. 840-845 (1985).
Shelton et al., "Addition of Halogens and Halogen Compounds to Allylic Chlorides. I. Addition of Hydrogen Halides," Journal of Organic Chemistry, 23, pp. 1876-1880 (1958).
Skell, et al., "Reactions of BrCl with alkyl radicals", Tetrahedron letters, vol. 27, No. 43, pp. 5181-5184, 1986.
Skell et al., "Selectivities of pi and sigma succinimidyl radicals in substitution and addition reactions, Response to Walling, Wi-Taliawi and Zhao", JACS, vol. 105, No. 15, Jul. 1, 1983, p. 5125-5131.
Tanuma et al., "Partially Fluorinated Metal Oxide Catalysts for a Friedel-Crafts-type Reaction of Dichlorofluoromethane with Tetrafluoroethylene", Catal. Lett. (2010) 136:77-82.
Tobey et al., "Pentachlorocyclopropane 1" Journal of the American Chemical Society, vol. 88, No. 11, Jun. 1, 1996 pp. 2478-2481.
Urry et al., "Free Radical Reactions of Diazomethane with Reactive Bromopolychloroalkane", JACS, vol. 86, No. 9, May 5, 1964, p. 1815-1819.
Wang Chin-Hsien, Elimination Reactions of polyhaloprppanes under emulsion catalytic conditions to give Halopropenes, Synthesis, Teorg Thieme Verlag, Stuttgart, De, vol. 1982, No. 6, Jan. 1, 1982, pp. 494-496.
Zhao et al., "Research Progress on Preparation Technology of 1, 1, 2, 3-Tetrachloropropene," Zhejiang Chemical Industry, vol. 41, No. 6, p. 8-10 (2010).
Zheng et al., "Review of the Preparation of the low GWP alternative 1,3,3,3-tetrafluoropropene", Zhejiang Huagong (2010) 41(3), 5-7.
Ochi, et al., "Preparation of Chloropropenes by Photochemical Dehydrochlorination of 1,2-Dichloropropane", Chemical Abstracts, Jul. 17, 1989, p. 574, 111(3).
Levanova, et al., "Choloriniation of Chloroolefins C3-C4", Doklady Chemistry, vol. 386, No. 4, 2002, 496-498.
Stevens, "Some New Cyclopropanes with a Note on the Exterior Valence Angles of Cyclopropane", JACS, Vo. 68, No. 4, 1945, 620-622.
Michigan Technological Univ., "Free-Radical Chlorination with Sulfuryl Chloride", Nov. 15, 2001, 1-7.

* cited by examiner

PROCESS FOR THE PRODUCTION OF CHLORINATED PROPANES AND PROPENES

This application is a 371 of PCT/US12/69230, filed Dec. 12, 2012, which claims benefit of 61/570,028, filed Dec. 13, 2011, and claims benefit of 61/583,799, filed Jan. 6, 2012.

FIELD

The present invention relates to processes for the production of chlorinated propanes and/or propenes. The processes are capable of providing useful intermediates with enhanced regioselectivity, while also producing undesirable byproducts at lower concentrations, than conventional processes.

BACKGROUND

Hydrofluorocarbon (HFC) products are widely utilized in many applications, including refrigeration, air conditioning, foam expansion, and as propellants for aerosol products including medical aerosol devices. Although HFC's have proven to be more climate friendly than the chlorofluorocarbon and hydrochlorofluorocarbon products that they replaced, it has now been discovered that they exhibit an appreciable global warming potential (GWP).

The search for more acceptable alternatives to current fluorocarbon products has led to the emergence of hydrofluoroolefin (HFO) products. Relative to their predecessors, HFOs are expected to exert less impact on the atmosphere in the form their lower GWP. Advantageously, HFO's also exhibit low flammability and low toxicity.

As the environmental, and thus, economic importance of HFO's has developed, so has the demand for precursors utilized in their production. Many desirable HFO compounds, e.g., such as 2,3,3,3-tetrafluoroprop-1-ene or 1,3,3,3-tetrafluoroprop-1-ene, may typically be produced utilizing feedstocks of chlorocarbons, and in particular, highly chlorinated propanes, e.g., tetra- and pentachloropropanes.

Unfortunately, these higher chlorides have proven difficult to manufacture using acceptable process conditions and in commercially acceptable regioselectivities and yields. For example, conventional processes for the production of pentachloropropanes provide unacceptable selectivity to the desired pentachloropropane isomer(s), i.e., 1,1,2,2,3-pentachloropropane, require the use of high intensity process conditions and/or catalyst systems that are difficult to utilize in large scale production processes and/or that are not recoverable once used. Other conventional processes may be limited to the addition of a single chlorine atom per reaction pass, and so must be repeated until the desired number of chlorine atoms has been added, with each additional step requiring additional capital, energy, and other cost investment. Still others require starting materials that are either cost prohibitive, have limited availability or both.

Further, the dehydrochlorination steps required to create alkenes from a feedstream comprising alkanes conventionally are conducted with the use of caustic, resulting in large quantities of waste water including low value by-products such as sodium chloride. Conventional processes rely on many such dehydrochlorination steps, thus multiplying the amount of waste water that must be treated prior to disposal.

It would thus be desirable to provide improved processes for the production of chlorocarbon precursors useful as feedstocks in the synthesis of refrigerants and other commercial products. More particularly, such processes would provide an improvement over the current state of the art if they provided a higher regioselectivity relative to conventional methods, required low intensity process conditions, and/or made use of catalyst systems and/or initiators that are recoverable or otherwise reusable, or were capable of the addition of multiple chlorine atoms per reaction pass as compared to conventional processes. Further advantages would be provided if lower cost and/or more widely available starting materials could be utilized.

BRIEF DESCRIPTION

The present invention provides efficient processes for the production of chlorinated propanes and/or propenes. Advantageously, the processes make use of 1,2-dichloropropane, a by-product in the production of chlorohydrin, as a low cost starting material. And, at least one chlorination step of the process is conducted with a catalyst that provides a regioselectivity of at least 5:1 to one chloropropane intermediate. In some embodiments, multiple chlorine atoms may be added per pass, while in others, the catalyst may be recoverable and reusable after the process. In some embodiments, further advantages may be provided by conducting one or more dehydrochlorinations catalytically, rather than with caustic. Less waste water is thus produced, and anhydrous HCl may be produced. Further cost savings are provided in that low intensity process conditions, e.g., low temperatures, low pressure and liquid phase reactions, are utilized. Finally, multiple chlorinations, involving multiple catalysts, may be conducted in the same reactor, providing capital and operating cost savings.

In one aspect, the present invention provides a process for the production of chlorinated propanes and/or propenes from a feedstream comprising 1,2-dichloropropane. At least one chlorination step of the process is conducted in the presence of a catalyst that provides a regioselectivity of at least 5:1, or at least 10:1, or at least 20:1, to one chloropropane intermediate. In some embodiments, the catalyst may comprise a Lewis acid, a nonmetallic iodide, an inorganic iodine salt, less than 10,000 ppm elemental iodine or combinations of these. The source of chlorine atoms may comprise either chlorine gas, sulfuryl chloride or both. The chlorinated propene may comprise from 3-4 chlorine atoms.

DETAILED DESCRIPTION

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). As used herein, percent (%) conversion is meant to indicate change in molar or mass flow of reactant in a reactor in ratio to the incoming flow, while percent (%) selectivity means the change in molar flow rate of product in a reactor in ratio to the change of molar flow rate of a reactant.

Reference throughout the specification to "one embodiment" or "an embodiment" means that a particular feature, structure, or characteristic described in connection with an embodiment is included in at least one embodiment. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

As used herein, the term "nonmetallic iodide" is meant to include any nonmetallic compound, incorporating, or otherwise capable of providing or forming in a reaction mixture, at least one hypervalent iodine species. Similarly, the term "inorganic iodine salt" is meant to include inorganic salt, incorporating, or otherwise capable of providing or forming in a reaction mixture, at least one hypervalent iodine species. The term "hypervalent", in turn, and as is understood by those of ordinary skill in the chemical arts, means a compound that may typically have one or more elements bearing more than eight electrons in their valence shells, and in particular iodine sources having oxidation states of greater than or equal to +1, e.g., +1, +3, +5, +7, etc. A precursor is a compound or composition that provides the active catalytic species in situ, for example, iron metal can form ferric chloride in environments comprising chlorine.

"PDC" may be used herein as an abbreviation for 1,2-dichloropropane, "TCP" may be used as an abbreviation for 1,2,3-trichloropropane and "TCPE" may be used as an abbreviation for 1,1,2,3-tetrachloropropene.

The present invention provides efficient processes for the production of chlorinated propanes and/or propenes. The present processes advantageously make use of a starting feedstream comprising 1,2-dichloropropane. PDC is readily available at low cost, at least because it is a by-product in many chlorohydrin processes. Conventionally, it is disposed of, typically via incineration, and so, using it as a starting material presents an opportunity to make use of an otherwise wasted material.

Further, in at least one chlorination step of the process, a catalyst that provides a regioselectivity of at least 5:1, or 8:1, or 10:1, or 15:1, or 20:1, or 30:1 or 40:1, or even 50:1, or greater, to one chloropropane relative to other chloropropane isomers having the same number of chlorine atoms is utilized. In some embodiments, for example, 1,1,2-trichloropropane may be provided at a regioselectivity of at least 20:1, relative to other trichloropropane isomers. In other embodiments, 1,1,2,2,3-pentachloropropane may be provided at a regioselectivity of at least 20:1 relative to other pentachloropropane isomers.

This high degree of selectivity is desirable in chloropropane intermediates, since production of predominantly desired intermediates can lead to regioselectivity to the desired chlorinated propene, which in some embodiments, may be 1,1,2,3-tetrachloropropene. Further, this high degree of regioselectivity has previously been provided only via extreme reaction conditions, e.g., high temperatures, e.g., greater than 100° C., high pressures, i.e., 100 psi over ambient and higher, and/or the use of vapor phase reactions. Such conditions may be undesirable not only because of the cost associated with the same, but also because they can result in reactor fouling due to product decomposition.

In contrast, the present processes utilize temperatures of less than 100° C. or less than 90° C., or less than 80° C., or less than 75° C., or less than 70° C., or even less than 65° C., or 60° C. Ambient pressures or pressures of at least 100 psi greater than ambient may be utilized. And, one or more reactions may be conducted in the liquid phase, so that evaporation of the reactants is not required, and thus reactor fouling may be minimized.

In some embodiments, a Lewis acid catalyst may be utilized to provide the desired regioselectivity to the chloropropane intermediate. In such embodiments, the Lewis acid catalyst may be utilized alone, and yet provide the desired regioselectivity to, e.g., 1,1,2-trichloropropane, particularly with 1,2-dichloropropane present in the feedstream.

Examples of Lewis acids capable of providing the recited regioselectivity include, but are not limited to, ferric chloride, antimony pentafluoride, boron trichloride, aluminum chloride and/or trichloride, and stannic chloride. Precursors to these, as well as any active decomposition products, may also be used. Combinations of two or more of these may also be used, if desired. In some embodiments, anhydrous aluminum chloride may desirably be utilized as the at least one Lewis acid.

In other embodiments, the regioselective catalyst may comprise iodine, and more specifically, may comprise a nonmetallic iodide and/or an inorganic iodine salt. While conventional processes that employ nonmetallic iodides are taught to be limited to the addition of single chlorine atoms, it has now been discovered that, nonmetallic iodides not only can add multiple chlorine atoms, but further, are capable of adding multiple chlorine atoms in a highly regioselective manner. Additionally, as a further indication of their catalytic action, little or no iodoalkane byproducts are produced when nonmetallic iodides are used as chlorination catalysts.

Any nonmetallic iodide can be used in the mixed catalyst system, and those of ordinary skill in the art are expected to be familiar with many. Suitable examples include, but are not limited to, iodobenzene, halogenated iodobenzenes, phenylchloroiodonium chloride, diaryliodonium salts, iodinated polymers, iodoxy compounds, iodoso compounds, iodine mono- and trihalides, iodine oxides, and derivatives or combinations of any number of these.

In other embodiments, one or more inorganic iodine salts may be utilized as the regioselective catalyst. Advantageously, in those embodiments wherein the process is conducted in a nonaqeuous media, the one or more inorganic iodine salts may be recovered in whole or in part, and/or reused.

Any inorganic iodine salt can be used as the regioselective catalyst, and those of ordinary skill in the art are expected to be familiar with many. Suitable examples include, but are not limited to, hypoiodites ($IO^-$), iodites ($IO_2^-$), iodates ($IO_3^-$), and/or periodates ($IO_4^-$), including mesoperiodates and orthoperiodates, or combinations of these. Specific examples of inorganic iodine salts include, but are not limited to sodium iodate, silver iodate, calcium iodate, potassium iodate, iodic acid, sodium periodate, potassium periodate, barium periodate, and periodic acid, and derivatives or combinations of any number of these.

In other embodiments, elemental iodine may be used, but at levels much lower than previously thought to be effective. That is, it has now been discovered that amounts of iodine much lower than conventionally utilized, i.e., 0.01 wt. %, provide improvements in yield and selectivity while yet not presenting the corrosion and volatility issues that may arise when these conventional levels are utilized. More specifically, amounts of elemental iodine of from 1 ppm to 5000 ppm, or from 5 ppm to 1000 ppm, or from 10 ppm to 100 ppm, have now surprisingly been discovered to provide selectivities to the desired chlorinated propanes and/or propenes of greater than 60%, in some cases greater than 70%, and in some cases greater than 80%. This is a significant improvement over processes wherein no iodine is used at all, wherein conversions of e.g., less than 60% can be seen. Since elemental iodine can be costly, significant cost savings are also provided by using the smaller amounts described herein. Combinations of one or more nonmetallic iodides, inorganic iodine salts and elemental iodine may also be used.

At least one regioselective catalysts is desirably used in the present process. Further, the at least one regioselective catalyst may be used in each chlorination step of the process, or in only one chlorination step, or any number of steps in between. All that is required is that at least one regioselective catalyst, i.e., the Lewis acid, nonmetallic iodide, inorganic iodide salt, and/or less than 10,000 ppm elemental iodine be employed in at least one chlorination step of the process.

In some embodiments, two or more of the regioselective catalysts may be utilized in the present process, either together as a mixed catalyst system, or consecutively. As is the case when one regioselective catalyst is used, the two or more regioselective catalysts may be utilized in one chlorination step of the process, two chlorination steps of the process, etc., or all chlorination steps of the process. For example, a Lewis acid may be used to catalyze the production of 1,1,2-trichloropropane from 1,2-dichloropropane, and then an iodine catalyst, i.e., a nonmetallic iodide, inorganic iodine salt, or less than 10,000 ppm elemental iodine, used to catalyze the production of 1,1,2,2,3-pentachloropropane thereafter. In such embodiments, both, or all, regioselective catalysts may be present in the reactor initially, or, added sequentially thereto.

If desired, some chlorination steps of the process may be carried out in the presence of conventional ionic chlorination catalysts or free radical initiators. Conventional ionic chlorination catalysts that may be used in the present process are known to those of ordinary skill in the art, and any of these may be used. Exemplary ionic chlorination catalysts include, but are not limited to, compounds comprising iron (ferric chloride), chlorine and sulfur, etc. If conventional ionic chlorination catalysts are to be utilized in one or more of the chlorination steps of the present process, the use of aluminum chloride can be preferred.

Suitable free radical chlorination catalysts include, but are not limited to, compounds comprising one or more azo-groups (R—N=N—R') such as azobisisobutyronitrile (AIBN) or 1,1'-azobis(cyclohexanecarbonitrile) (ABCN) and organic peroxides such as di-tert-butyl peroxide, dibenzoyl peroxide, benzoyl peroxide, methyl ethyl ketone peroxide, and acetone peroxide. In some embodiments, the use of benzoyl peroxide may be preferred, either alone or in combination with UV or visible light or heat. Such catalysts may also enhance the chlorination of double bonds in olefins or chlorinated olefins to produce $\alpha$, $\beta$ dichloroalkanes.

The chlorinated propanes produced via the chlorination step(s) can be converted to propenes in any known fashion, such as via one or more dehydrochlorination reactions or steps. Any such dehydrochlorination steps may be conducted in the presence of an inorganic base such as a liquid phase caustic. Many chemical bases are known in the art to be useful for this purpose, and any of these can be used. For example, suitable bases for dehydrochlorination include, but are not limited to, alkali metal hydroxides, such as sodium hydroxide, potassium hydroxide, calcium hydroxide; alkali metal carbonates such as sodium carbonate; lithium, rubidium, and cesium or combinations of these. Phase transfer catalysts such as quaternary ammonium and quaternary phosphonium salts can also be added to improve the dehydrochlorination reaction rate with these chemical bases.

Alternatively, in some embodiments, one or more dehydrochlorination steps utilized in the process may be carried out in the presence of a catalyst so that the reaction rate is enhanced and also use of liquid caustic is reduced, or even eliminated, from the process. If the use of catalysts is desired, suitable dehydrochlorination catalysts include, but are not limited to ferric chloride ($FeCl_3$) and aluminum chloride ($AlCl_3$). Ferric chloride, for example, can be used to dehydrochlorinate 1,1,1,2,3-pentachloropropane to TCPE.

Any or all of the chlorination and/or dehydrochlorination catalysts can be provided either in bulk or in connection with a substrate, such as activated carbon, graphite, silica, alumina, zeolites, fluorinated graphite and fluorinated alumina.

Generally speaking, and whatever the regioselective catalyst, other chlorination catalyst or dehydrochlorination catalyst(s) employed, enough of the catalyst should be utilized to provide some improvement to reaction process conditions (e.g., a reduction in required temperature) and desirably, reaction selectivity, but yet not be more than will provide any additional benefit, if only for reasons of economic practicality.

For purposes of illustration only, then, it is expected that useful concentrations of a regioselective catalyst comprising a Lewis acid, in a batch process, will range from 0.001% to 20% by weight each with respect to dichloropropane, or from 0.01% to 10%, or from 0.1% to 5 wt. %, inclusive of all subranges therebetween. Suitable batch process concentrations of a regioselective catalyst comprising a nonmetallic iodide are expected to range from 0.001% to 80% by weight with respect to the dichloropropane, or from 0.01% to 60%, or from 0.1% to 40 wt. %, inclusive of all subranges therebetween. Useful concentrations of a regioselective catalyst comprising an inorganic iodine salt, in a batch process, will range from 0.001% to 40% by weight with respect to the alkane, or from 0.01% to 30%, or from 0.1% to 20 wt. %, inclusive of all subranges therebetween. Surprisingly low levels of elemental iodine are effective, e.g., from 1 ppm to 5000 ppm, or from 5 ppm to 1000 ppm, or from 10 ppm to 100 ppm.

If a dehydrochlorination catalyst, e.g., $FeCl_3$, is utilized, useful concentrations may range from 0.01 wt % to 5 wt. %, or from 0.05 wt % to 2 wt % at temperature of 70° C. to 200° C. If a chemical base is utilized for one or more dehydrochlorinations, useful concentrations of these will range from 0.01 to 20 grmole/L, or from 1 grmole/L to 10 grmole/L, inclusive of all subranges therebetween.

Chlorine atoms are desirably supplied to the process by either chlorine, sulfuryl chloride, or both. In the case of embodiments wherein sulfuryl chloride ($SO_2Cl_2$) is utilized as a chlorine source, advantages can be seen in that sulfuryl chloride can also act as a solvent for the regioselective catalysts and/or reactions, thereby assisting in the provision of an acceptable reaction rate and/or yield. And, the sulfuryl chloride may be regenerated, if desired. On the other hand, in those embodiments wherein regeneration of sulfuryl chloride may prove unwieldy or otherwise be undesirable, chlorine may utilized, either alone or in conjunction with an appropriate solvent, such as, e.g., carbon tetrachloride and/or 1,2,3-trichloropropane. In such embodiments, lesser concentrations of the chlorine source can be required, at least since chlorine is not also acting as a solvent. Further, the regioselective catalyst may retain its activity for a longer period of time in those embodiments wherein chlorine gas is used as the chlorine source as opposed to sulfuryl chloride.

The reaction conditions under which the process is carried out are advantageously low intensity. That is, low temperatures, e.g., of less than 100° C., or less than 90° C., or less than 80° C. or less than 70° C., or less than 60° C., may be utilized and the desired selectivities to the desired chlorinated alkenes yet be realized. In some embodiments, temperatures of from 40° C. to 90° C., or from 50° C. to 80° C., or from 55° C. to 75° C., may be utilized. Similarly, ambient pressure is suitable for carrying out the process, or pressures within 300, or 200, or 100, or 50, or 40, or 30, or 20, or even 10 psi, of ambient are suitable. Reactor residence time may also be minimized with the desired selectivities yet seen—for example, reactor occupancy times of less than 15 hours, or less than 10 hours, or less than 9, 8, 7, 6, or even 5 hours, are possible. The reactor may be any suitable liquid phase reactor, such as a batch or continuous stirred tank autoclave reactor with an internal cooling coil. A shell and multitube exchanger followed by vapor liquid disengagement tank or vessel can also be used.

That being said, the particular conditions employed at each step described herein are not critical, nor is the sequence of reaction steps, and these are readily determined by those of ordinary skill in the art. Those of ordinary skill in the art will readily be able to determine the particular conditions at which to operate the distillation/fractionation, drying, dehydrochlorination and isomerization steps described herein, as well as the appropriate order of the steps to arrive at the desired chlorinated propene. What is important is that PDC is utilized as a starting material, and at least one chlorination step is conducted in the presence of one or more catalysts that provide a regioselectivity to one chloropropane of at least 5:1 relative to other chloropropanes. In some embodiments, provisions may also be made for the recovery of anhydrous HCl.

In the present process, dichloropropane is converted to a chlorinated alkene, e.g., TCPE, using a series of consecutive chlorination and dehydrochlorination steps. In one exemplary embodiment, PDC is fed to a liquid phase chlorination reactor, e.g., such as a batch or continuous stirred tank autoclave reactor with an internal cooling coil. A shell and multitube exchanger operating in plug flow, followed by vapor liquid disengagement tank or vessel can also be used. Suitable reaction conditions include, e.g., a temperature of from 30° C. to 150° C., a pressure of from 100 kPa to 2000 kPa. The reaction is carried out in the presence of one or more regioselective catalysts that provide a regioselectivity to, e.g., 1,1,2-trichloropropane of at least 5:1 over other trichloropropane isomers.

Some embodiments of the invention will now be described in detail in the following examples.

Example 1

Ionic Chlorination of PDC to Trichloropropanes Using Aluminum Chloride as Regioselective Catalyst and Sulfuryl Chloride as Chlorinating Agent Liquid sulfuryl chloride and PDC (1,2-dichloropropane) are mixed in a 100 ml flask heated in a water bath to maintain temperature 55° C.-60° C. in the presence of 40 mole % of $AlCl_3$. A reflux column is placed to return unreacted reactants as well the reaction intermediate 1-chloropropene to the reaction liquid while the HCl and $SO_2$ byproducts are released to a caustic scrubber at the top of the reflux column. Gas chromatography coupled with mass spectrometry is used to determine the product composition.

After 30 minutes of reaction time the product mixture was found to be 1,1,2-trichloropropane and 1,2,3-trichloropropane at molar ratio of 40 to 1.

Example 2

Ionic Chlorination of 1,2-Dichloropropane to 1,1,2,2,3-Pentachloropropane Using Aluminum Chloride as Regioselective Catalyst and Sulfuryl Chloride as Chlorinating Agent Liquid sulfuryl chloride and 1,2-dichloropropane are mixed in a 100 ml flask heated in a water bath to maintain temperature 55° C.-60° C. in the presence of 40 mole % $AlCl_3$ catalyst. A reflux column is placed to return unreacted reactants as well the reaction intermediates to the reaction liquid while the HCl and $SO_2$ byproducts are released to a caustic scrubber at the top of the reflux column. Gas chromatography coupled with mass spectrometry is used to determine the product composition.

After 17 hours of reaction time the product mixture was found to contain 1,1,2,2,3-pentachloropropane as the only pentachloropropane.

Example 3

Chlorination of 1,1,2-trichloropropane to 1,1,2,2,3-pentachloropropane Using Iodobenzene and Aluminum Chloride as Regioselective Catalyst and Sulfuryl Chloride as Chlorinating Agent A product stream containing 26 wt % 1,1,2-trichloropropane, 61 wt % sulfuryl chloride, and 12 wt % aluminum chloride based upon the total weight of the initial reaction mixture is charged with 10 mole % aluminum chloride dissolved in 310 mole % sulfuryl chloride followed by 10 mole % iodobenzene wherein the mole % are with respect to 1,1, 2-trichloropropane. The resulting mixture is stirred for 4 hours at a temperature of 70° C. and then cooled to ambient temperature prior to pouring the mixture into an ice bath. The resulting solution is filtered to remove the quenched catalyst byproduct and the resulting product mixture is analyzed by gas chromatography. The final organic phase is found to consist of >91% 1,1,2,2,3-pentachloropropane, with the remaining 9% comprising a mixture of tri-, tetra-, and hexachloropropane isomers.

Example 4

Chlorination of 1,1,2-trichloropropane to 1,1,2,2,3-pentachloropropane Using Iododurene (2,3,5,6-tetramethyl-1-iodobenzene) and Aluminum Chloride as Regioselective Catalysts and Sulfuryl Chloride as Chlorinating Agent A product stream containing 26 wt % 1,1,2-trichloropropane, 61 wt % sulfuryl chloride, and 12 wt % aluminum chloride based upon the total weight of the initial reaction mixture is charged with 10 mole % aluminum chloride dissolved in 200 mole % sulfuryl chloride followed by 10 mole % iododurene, wherein all mole % s are with respect to 1,1,2-trichloropropane. The resulting mixture is allowed to stir for 3 hours at a temperature of 70° C. and then cooled to ambient temperature prior to pouring the mixture into an ice bath. The resulting solution is filtered to remove the quenched catalyst byproduct and the resulting product mixture is analyzed by gas chromatography. The final organic phase is found to consist of >84% 1,1,2,2,3-pentachloropropane, with the remaining 16% comprising a mixture of tri-, tetra-, and hexa-chloropropane isomers.

Example 5

Chlorination of 1,2-Dichloropropane to 1,1,2,2,3-Pentachloropropane Using Sodium Periodate and Aluminum Chloride as Regioselective Catalysts and Sulfuryl Chloride as Chlorinating Agent 17 g sulfuryl chloride and 2.5 g aluminum chloride is charged to a reactor equipped with a magnetic stir bar and reflux condenser. The reaction mixture is heated to 60° C. and then 4.1 g of 1,2-dichloropropane is charged. The reaction is stirred for 35 minutes, where GC analysis indicated that >99% of the 1,2-dichloropropane had been reacted to form primarily 1,1,2-trichloropropane.

An additional 15 g of sulfuryl chloride along with 1 g of sodium periodate is added. The reaction is allowed to react for a total 4 hours before being cooled back to ambient temperature. The crude reaction mixture is filtered to collect the sodium periodate catalyst as a wet cake that is washed with methylene chloride to give 0.8 g of recovered sodium periodate.

The reaction mixture and methylene chloride wash are combined, slowly poured into an ice water bath, and allowed to stir until quenched. The organic and aqueous phases are separated and the aqueous phase is extracted with an equal volume of methylene chloride. The combined organic fractions are dried over magnesium sulfate, the excess solvent is removed by rotary evaporator, and the final product is isolated as a colored oil.

GC and NMR analysis of the final product mixture shows a yield of 4.7 g of 1,1,2,2,3-pentachloropropane, 0.7 g of tetrachloropropane isomers, 0.4 g of 1,1,2-trichloropropane, 0.3 g of hexachloropropane isomers, and 0.2 g of 1,2,3-trichloropropane.

Example 6

Chlorination of 1,2-Dichloropropane to 1,1,2,2,3-Pentachloropropane Using Aluminum Chloride and Recovered Sodium Periodate as Regioselective Catalysts and Sulfuryl Chloride as Chlorinating Agent 9.3 g sulfuryl chloride and 1.3 g aluminum chloride is charged to a reactor equipped with a magnetic stir bar and reflux condenser. The reaction mixture is heated to 60° C. and charged with 2.3 g of 1,2-dichloropropane. The reaction is stirred for 35 minutes, when GC analysis indicates that >99% of the 1,2-dichloropropane has reacted to form primarily 1,1,2-trichloropropane.

An additional 7.9 g of sulfuryl chloride along with 0.5 g of sodium periodate recovered from Example 5 is charged. The reaction is allowed to react for a total of 4 hours before being cooled back to ambient temperature. The crude reaction mixture is filtered to collect the sodium periodate catalyst as a wet cake that is washed with methylene chloride to give 0.45 g of recovered sodium periodate.

The reaction mixture and methylene chloride wash are combined, slowly poured into an ice water bath, and allowed to stir until quenched. The organic and aqueous phases are separated and the aqueous phase is extracted with an equal volume of methylene chloride. The combined organic fractions are dried over magnesium sulfate, the excess solvent is removed by rotary evaporator, and the final product is isolated as a colored oil.

GC and NMR analysis of the final product mixture shows a yield of 3.1 g of 1,1,2,2,3-pentachloropropane, 0.5 g of hexachloropropane isomers, 0.1 g of 1,2,3-trichloropropane, and 0.1 g of tetrachloropropane isomers.

Example 7

Chlorination of 1,2-Dichloropropane to 1,1,2,2,3-Pentachloropropane Using Sodium Iodate and Aluminum Chloride as Regioselective Catalysts and Sulfuryl Chloride as Chlorinating Agent 17 g sulfuryl chloride and 2.5 g aluminum chloride is charged to a reactor equipped with a magnetic stir bar and reflux condenser. The reaction mixture is heated to 60° C. and then 4.1 g of 1,2-dichloropropane is charged. The reaction is allowed to stir for 35 minutes, when GC analysis indicates that >99% of the 1,2-dichloropropane has reacted to form primarily 1,1,2-trichloropropane.

An additional 15 g of sulfuryl chloride along with 0.5 g of sodium iodate is charged. The reaction is allowed to react for a total 4 hours before being cooled back to ambient temperature. The reaction mixture is slowly poured into an ice water bath and allowed to stir until quenched. The organic and aqueous phases are separated and the aqueous phase is extracted with an equal volume of methylene chloride. The sodium iodate is recovered in the aqueous wash as indicated by ion chromatography analysis. The combined organic fractions are dried over magnesium sulfate, the excess solvent is removed by rotary evaporator, and the final product was isolated as a colored oil.

GC and NMR analysis of the final product mixture shows a yield of 5.4 g of 1,1,2,2,3-pentachloropropane, 0.6 g of tetrachloropropane isomers, 0.4 g of hexachloropropane isomers, 0.3 g of 1,1,2-trichloropropane and 0.2 g of 1,2,3-trichloropropane.

Example 8

Chlorination of 1,2-Dichloropropane to 1,1,2,2,3-Pentachloropropane Using Sodium Iodate and Aluminum Chloride as Regioselective Catalysts and Sulfuryl Chloride as Chlorinating Agent 17 g sulfuryl chloride, 0.6 g aluminum chloride, and 0.8 g of sodium iodate is charged to a reactor equipped with a magnetic stir bar and reflux condenser. The reaction mixture is heated to 60° C. and then 4.1 g of 1,2-dichloropropane is added. The reaction is allowed to stir for a total 4 hours before being cooled back to ambient temperature.

The reaction mixture is slowly poured into an ice water bath and allowed to stir until quenched. The organic and aqueous phases are separated and the aqueous phase is extracted with an equal volume of methylene chloride. The sodium iodate is recovered in the aqueous wash as indicated by ion chromatography analysis. The combined organic fractions are dried over magnesium sulfate, the excess solvent is removed by rotary evaporator, and the final product is isolated as a colored oil.

GC and NMR analysis of the final product mixture shows a yield of 2.3 g of 1,1,2,2,3-pentachloropropane, 1.4 g of 1,1,2-trichloropropane, 0.9 g of tetrachloropropane isomers, 0.8 g of 1,2,3-trichloropropane, and 0.2 g of hexachloropropane isomers.

Example 9

Chlorination of 1,2-Dichloropropane to 1,1,2,2,3-Pentachloropropane Using Aluminum Chloride as Regioselective Catalyst and Chlorine as Chlorinating Agent 1,2-dichloropropane (10 mL) is added to a solution of carbon tetrachloride (37.2 mL) containing aluminum trichloride (0.51 g). The mixture is stirred while chlorine (30% v/v in nitrogen) is passed through the solution while the mixture is held at 50° C. for 3 hr and then at 100° C. for 1 hr. The pressure of the system was maintained between 60-100 psig throughout the reaction. Analysis of the reaction mixture via $^1$H NMR spectroscopy revealed that 1,2-dichloropropane was nearly consumed within 3 hr at 50° C. producing 1,1,2-trichloropropane as the major product. After additional 1 hr and 100° C., the analysis of the final mixture identified 1,1,2,2,3-pentachloropropane as the major product.

Example 10

Chlorination of 1,2-dichloropropane to 1,1,2,2,3-pentachloropropane Using Aluminum Chloride and Low Levels of Elemental Iodine as Regioselective Catalysts and Chlorine as Chlorinating Agent A product stream is prepared by feeding chlorine gas at 30 sccm through a starting mixture of 22.6 wt % 1,2-dichloropropane, 1.3 wt % aluminum chloride, and 76.1 wt % methylene chloride at 130 psig and 70° C. until GC analysis indicates that the starting dichloropropane has undergone 68% conversion to give 1,1,2-trichloropropane as the major intermediate species. This stream is charged with 35 ppm elemental iodine dissolved in 15 mL of methylene chloride based on initial dichloropropane within the reaction mixture. The resulting mixture is allowed to stir until 36.1% conversion of the 1,1,2-trichloropropane intermediate is observed to give the desired pentachloropropane as the major isomer. Furthermore, the desired pentachloropropane and its precursor 1,2,2,3-tetrachloropropane in 82.3% selectivity over the undesired byproducts of 1,1,2,2,3,3-hexachloropropane and 1,1,2,3-tetrachloropropane.

The invention claimed is:

1. A process for the production of chlorinated propanes and/or propenes from a feedstream comprising 1,2-dichloropropane comprising catalyzing at least one chlorination step with one or more regioselective catalysts that provide a regioselectivity to one chloropropane of at least 5:1 relative to other chloropropanes.

2. The process of claim 1, wherein the regioselective catalyst comprises aluminum chloride.

3. The process of claim 1, wherein the regioselective catalyst comprises a nonmetallic iodide, an inorganic iodine salt, or less than 10,000 ppm elemental iodine.

4. The process of claim 3, wherein the regioselective catalyst comprises a nonmetallic iodide comprising one or more iodobenzenes or halogenated iodobenzenes, phenylchloroiodonium chloride, diaryliodonium salts, iodinated polymers, iodoxy compounds, iodoso compounds, iodine mono- and trihalides, iodine oxides, and derivatives or combinations of any number of these.

5. The process of claim 3, wherein the regioselective catalyst comprises an inorganic iodine salt comprising sodium iodate, sodium periodate, or combinations of these.

6. The process of claim 1, wherein at least two chlorination steps are catalyzed with the regioselective catalyst.

7. The process of claim 6, wherein one chlorination step is catalyzed with aluminum chloride, and another step is catalyzed with a nonmetallic iodide, an inorganic iodine salt or less than 10,000 ppm elemental iodine.

8. The process of claim 7, wherein both steps are conducted in the same reactor.

9. The process of claim 1, wherein at least one chlorination step is conducted in the presence of a free radical initiator or ionic chlorination catalyst, wherein the free radical initiator comprises azobisisobutyronitrile, 1,1'-azobis(cyclohexanecarbonitrile), di-tert-butyl peroxide, benzoyl peroxide, dibenzoyl peroxide, methyl ethyl ketone peroxide, acetone peroxide, or a combination of any number of these.

10. The process of claim 1, further comprising at least one dehydrochlorination step.

11. The process of claim 10, wherein the at least one dehydrochlorination step is conducted in the presence of a catalyst.

12. The process of claim 1, wherein the source of chlorine atoms comprises either sulfuryl chloride, chlorine or a combination of these.

13. The process of claim 12, wherein the process is further conducted in the presence of a solvent comprising carbon tetrachloride and/or sulfuryl chloride.

14. The process of claim 1, wherein the one chloropropane is a tri-, or pentachloropropane comprising 1,1,2-trichloropropane, 1,1,2,2,3-pentachloropropane or a combination of these.

15. The process of claim 1, wherein the chlorinated propene comprises 1,1,2,3-tetrachloropropene.

16. The process of claim 1, wherein the chlorination step occurs at ambient pressure.

* * * * *